(12) United States Patent
Russell

(10) Patent No.: US 6,791,086 B2
(45) Date of Patent: Sep. 14, 2004

(54) MICROSPECTROMETER GAS ANALYZER

(75) Inventor: James T Russell, Bellevue, WA (US)

(73) Assignee: Respironics, Inc., Murrysville, PA (US)

( * ) Notice: Subject to any disclaimer, the term of this patent is extended or adjusted under 35 U.S.C. 154(b) by 56 days.

(21) Appl. No.: 10/227,135

(22) Filed: Aug. 23, 2002

(65) Prior Publication Data

US 2003/0043373 A1 Mar. 6, 2003

Related U.S. Application Data

(60) Provisional application No. 60/316,763, filed on Aug. 31, 2001.

(51) Int. Cl.[7] .................................................. G01J 3/18
(52) U.S. Cl. ................. 250/339.07; 250/351; 250/353; 356/305; 356/328
(58) Field of Search .................. 250/339.07, 339.01, 250/347, 353; 359/197, 199; 356/305, 328, 330

(56) References Cited

U.S. PATENT DOCUMENTS

| | | | |
|---|---|---|---|
| 4,320,971 A | 3/1982 | Hashimoto et al. | |
| 4,961,646 A | 10/1990 | Schrammli et al. | |
| 5,451,787 A | 9/1995 | Taylor | |
| 5,731,874 A | 3/1998 | Maluf | |
| 5,801,826 A | 9/1998 | Williams | |
| 5,807,750 A | 9/1998 | Baum et al. | |
| 5,880,834 A | 3/1999 | Chrisp | |
| 5,905,571 A | 5/1999 | Butler et al. | |
| 5,999,319 A | 12/1999 | Castracane | |
| 6,039,697 A | 3/2000 | Wilke et al. | |
| 6,201,629 B1 | 3/2001 | McClelland et al. | |
| 6,249,346 B1 | 6/2001 | Chen et al. | |

Primary Examiner—Albert Gagliardi
(74) Attorney, Agent, or Firm—Michael W. Haas

(57) ABSTRACT

A robust, compact spectrometer apparatus for determining respective concentrations or partial pressures of multiple gases in a gas sample with single as well as multiple and even overlapping, absorption or emission spectra that span a wide spectral range.

70 Claims, 6 Drawing Sheets

MICROSPECTROMETER GAS ANALYZER

CROSS-REFERENCE TO RELATED APPLICATIONS

This application claims priority from U.S. Provisional Application Serial No. 60/316,763, filed Aug. 31, 2001 under the provisions of 35 U.S.C. §119(e), the contents of which are hereby incorporated by reference in their entirety.

BACKGROUND OF THE INVENTION

1. Field of the Invention

This invention relates to a method and apparatus for efficiently and robustly measuring gas concentrations/partial pressure of respiratory and anesthetic gases.

2. Description of the Related Art

It is well known by those of ordinary skill in the art that gas analyzers of the nondispersive infrared (NDIR) type operate on the principle that the concentration of specific gases can be determined by (a) directing infrared radiation (IR) through a sample of a gaseous mixture, (b) separately filtering this infrared radiation to minimize the energy outside the band absorbed by each specific gas (c) measuring the filtered radiation impinging upon one or more detecting devices and (d) relating a measure of the infrared absorption of each gas to its concentration. Gases that may be measured exhibit increased absorption (and reduced transmittance) at specific wavelengths in the infrared spectrum such that, the greater the gas concentration, the proportionally greater absorption and lower transmittance. An extension of this NDIR technique uses a continuous, linear bandpass filter, followed by a linear array of detectors.

Gas analyzers are widely used in medical applications and may be characterized as being located either in the main path of the patient's respiratory gases (mainstream analyzers) or in an ancillary path usually paralleling the main path (sidestream analyzers). A mainstream analyzer is situated such that the subject's inspired and expired respiratory gases pass through an airway adapter onto which the analyzer is placed. Mainstream designs require the optical and electronic components to be interfaced to a patient's airway or to a respiratory circuit in communication with a patient in a location in relatively close proximity to the patient. As a result, to be accepted in clinical use, the mainstream gas analyzer must be designed as a compact, lightweight yet robust structure unaffected by typical mechanical abuse and temperature variations associated with prolonged use in health care facilities.

While conventional mainstream gas analyzers work well for a small number of specific, non-overlapping spectrum wavelengths, it is difficult to change wavelengths of interest. The system becomes increasingly inefficient if there are more than 2 or 3 wavelengths of interest, and it is very difficult and expensive to provide resolutions significantly better than 0.1 micron, FWHM (full-width at half maximum) in the IR region.

It is known to use grating spectrometers for gas analysis. There are two general configurations of grating spectrometers: the spectrograph, which originally spreads the spectrum out over a strip of photographic film or a linear array detector, and the spectrometer, which uses a single detector that is set at an appropriate location or angle to register a particular spectral element.

For IR gas measurements, an IR source provides broadband energy that is collimated and passed through a gas sample cell. The collimated broadband energy, now attenuated at certain wavelengths, is directed to a diffraction grating where it is diffracted from the grating, spread out into a continuous spectrum, and focused with a mirror onto a small detector. The diffraction grating is rotated about an axis parallel to the grating lines, and substantially coaxial with the face of the diffraction grating. As the diffraction grating is rotated, the spectrum is scanned past the single detector. Since the diffraction grating rotation is synchronized with the detector readout electronics, specific, but arbitrary, spectrum features can be isolated and registered.

One major drawback of many conventional spectrometers is that the rotation of the diffraction grating requires a motor of some sort, oscillating linkages to drive the diffraction grating from the motor, and a bearing assembly. While such an arrangement can deliver good results, such a structure is relatively large, heavy and expensive. Other conventional spectrometers use an oscillating motor, sometimes called a galvanometer drive, in place of the motor and linkage. Such arrangements are less expensive, but still large, heavy and relatively expensive.

U.S. Pat. No. 6,249,346 (2001) to Chen, et al., U.S. Pat. No. 6,039,697 (2000) to Wilke, et al., and U.S. Pat. No. 5,931,161 (1999) to Keilbach, et al. all disclose relatively smaller sized spectrometers, but of designs that are of undue bulk and, in some instances, complexity.

SUMMARY OF THE INVENTION

Accordingly, it is an object of the present invention to provide a spectrometer that overcomes the shortcomings of conventional gas analyzing devices. This object is achieved according to one embodiment of the present invention by providing a robust spectrometer apparatus for determining respective concentrations or partial pressures of multiple gases in a gas sample with single, as well as multiple and even overlapping, absorption or emission spectra that span a wide spectral range.

The present invention adapts a grating spectrometer for use in a compact respiratory gas analysis instrument. Specifically, the present invention employs a scanning spectrometer, which scans, or sweeps, the spectrum across a fixed detector. From an optical point of view, this apparatus may be characterized as a modified Ebert scanning monochrometer.

A very small, inexpensive oscillating mirror may be made using a MEMS (MicroElectroMechanical System) fabrication process. With a diffraction grating added to the mirror surface, this structure provides a very low cost, small, lightweight but rugged scanner for an in-line IR gas analysis instrument.

Spectrum resolution is primarily a function of the grating size, aperture, line pitch, diffraction order, and collimation. In the present invention, the required grating width is in the 1 to 2 mm range, which is well suited to existing MEMS technology. The other parameters are easily obtained or controlled, at least well enough for necessary accuracy.

The diffraction grating may be formed separately and glued on to the "mirror" surface or, preferentially, the diffraction grating may be formed in the surface of the mirror as part of the MEMS fabrication processing. The drive to make the mirror oscillate may be magnetic, wherein the mirror either has a planar coil formed on the back or the mirror itself is made magnetic or, alternatively, the mirror may be driven electrostatically. Because the required angular amplitude is relatively small, an electrostatic drive is currently preferred.

The apparatus of the present invention may also be configured in several additional ways. In one instance, the oscillating grating may be removed and replaced by a scanning (oscillating) mirror. In an embodiment of this approach, the mirror scans the input light over a fixed grating, which disperses the spectrum. As before, the spectrum is focused by a mirror onto the detector plane. While this alternative method requires one additional component, the manufacturing cost may be less because the MEMS oscillating element does not need to have a grating fabricated on its surface.

In yet another alternative embodiment, the oscillating mirror may be positioned to direct the attenuated broadband energy beam back through the gas sample cell, with the grating and detector on the same side of the gas sample cell as the IR source. The advantage of this arrangement is higher sensitivity (due to the double pass through the gas in the cell), and a somewhat narrower package. Alternatively, in the double pass configuration, the mirror on the side opposite to the source may be fixed, and an oscillating mirror/fixed grating (or oscillating grating) and detector system located on the source side. These various embodiments may be configured in a single plane or the oscillating mirror, scanning grating or a focusing mirror may be rotated in orientation to direct the beam in a different plane, so that different package configurations may be easily accommodated.

A diffraction grating can provide diffracted beams in several orders. Ordinarily, the first order is used, either + or −1, and the shape of the grooves in the grating are designed to emphasize the chosen order. However, there can be some residual energy in higher orders. The result is that spectral regions at a shorter wavelength may overlap the first order spectrum. This problem may be solved, as required, with a blocking filter set to cut off all wavelengths that are outside of a spectral region of interest.

Data processing electronics for the apparatus of the present invention are synchronized with the motion of the scanning element. One approach is to extract a timing signal from the mirror drive. Alternatively, the mirror may have coils or magnetic or piezoelectric sensors mounted on it to provide signals indicative of a substantially instantaneous location of a portion of the mirror for use in synchronization. Another sensing technique for using in synchronization is to reflect an auxiliary beam off the front or back of the mirror to a separate detector. A currently preferred technique is to use a unique feature of the detected spectrum, if such is available or provided. Assuming that the mirror is resonant, there will be relatively long periods when the detector will not receive any signal. This is because the scan will be more easily interpreted if it is in the more nearly linear part of the scan, and because the blocking filter will remove all signals prior to, or following, the spectral region of interest. As such, the long blank period followed by a sharp rise in signal may be used to provide a suitably unique marker to a phase lock loop synchronizer. The blank period also provides a background light condition so that the detector zero may be set. Full scale can be implied by any spectral region between absorption peaks, or regions where known peaks have been subtracted.

Note that because the data generated by the apparatus is continuous, it is believed to be possible to incrementally subtract known, and previously stored, specific spectral lines, i.e., "peel off" individual lines, one by one. Such processing improves separation, or reduces interference, especially of weak lines.

These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE PRESENTLY PREFERRED EMBODIMENTS OF THE INVENTION

Figure 1A:
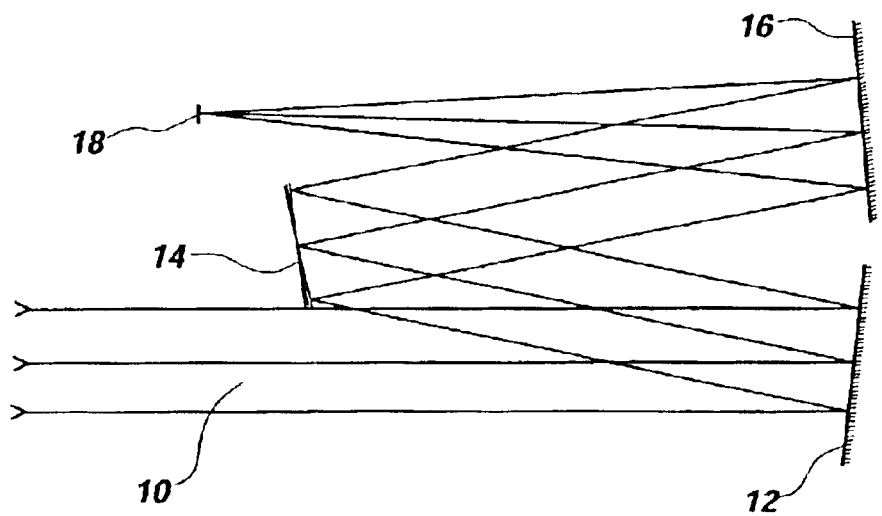
FIG. 1A is a schematic optical system layout for a spectrometer with an oscillating scanner mirror-diffraction grating combination according to the principles of the present invention.

FIG. 1A is a schematic optical layout for a spectrometer according to the principles of the present invention. Energy in the form of a light beam 10, such as an infrared beam, proceeds from a sample cell G (see FIG. 1B) and strikes a turning mirror 12. Turning mirror 12 then reflects light beam 10 towards scanning grating reflector 14, which may also be termed a scanning mirror. It should be noted that scanning grating reflector 14 oscillates about an axis perpendicular to the page (the oscillations are shown in an exaggerated form). From the scanning grating reflector 14, the now-dispersed light beam 10 travels to a focusing mirror 16 which, in turn, focuses light beam 10 to the detector 18 which includes, or has associated therewith, appropriate readout circuitry. Detector 18 may comprise, for example, a slit- or pinhole-defined detector, as known in the art.

Figure 1B:
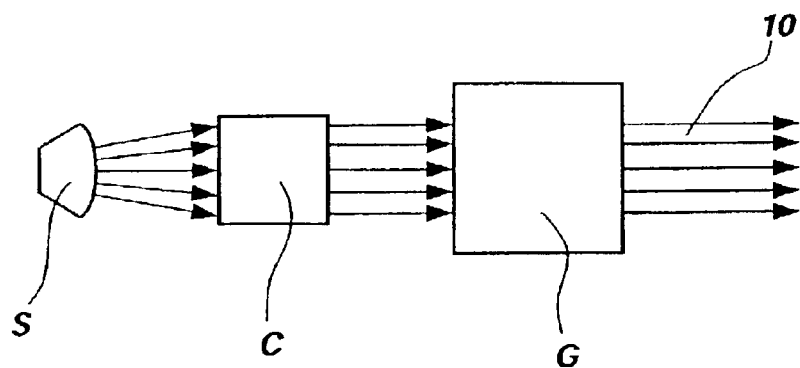
FIG. 1B is a schematic diagram of the spectrometer in which the optical system of FIG. 1A can be suitably employed.

FIG. 1B schematically illustrates the complete the structure of a spectrometer for use with the various optical embodiments of the present invention. As shown in FIG. 1B, an infrared light source S emits an infrared beam which may be collimated using source optics or a collimator C, as shown. The collimated infrared beam then enters gas sample cell G, exiting same to turning mirror 12. Such an arrangement may be used with all of the described embodiments herein, except it is notable that the embodiments of FIGS. 5A through 5C do not require the presence of a collimator C or source optics to collimate the infrared beam.

Figure 2:
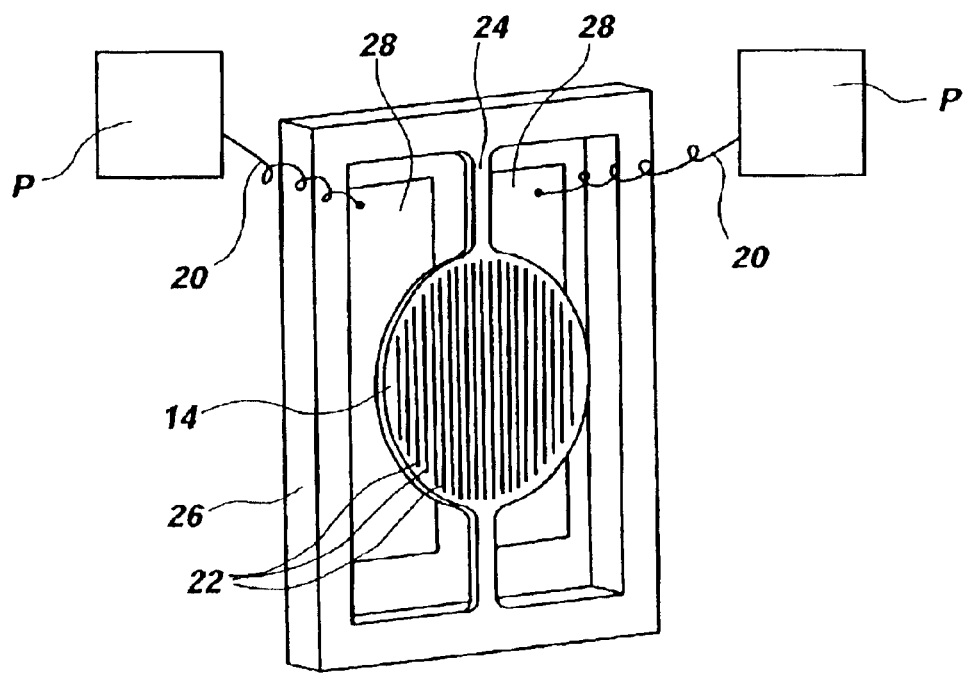
FIG. 2 is a perspective view of an oscillating mirror/grating combination suitable for use in the optical system of FIG. 1A.

Referring to FIG. 2, scanning grating reflector 14 has diffraction grating lines 22 positioned on it. The lines may be glued on or machined into the reflective, mirror surface using a MEMS process, or they may be positioned through some other known technique. U.S. Pat. No. 6,201,269 to McClelland, et al., the disclosure of which is incorporated herein by reference, discloses a suitable MEMS process for fabricating an oscillating mirror, which process may be adapted to fabricate scanning grating reflector 14. Scanning grating reflector 14 has a flexure axis 24 parallel to diffraction lines 22 and is mounted to a frame 26 through support members coaxial with flexure axis 24. Backings 28 may be electrically conductive so as to provide an electrostatic drive for scanning grating reflector 14 when leads 20 are connected between backing 28 and a suitable power source P as known in the art. Two power sources P are depicted for simplicity in FIG. 2 although, of course, a single power source P may be used to power backings 28 in alternation.

Figure 3:
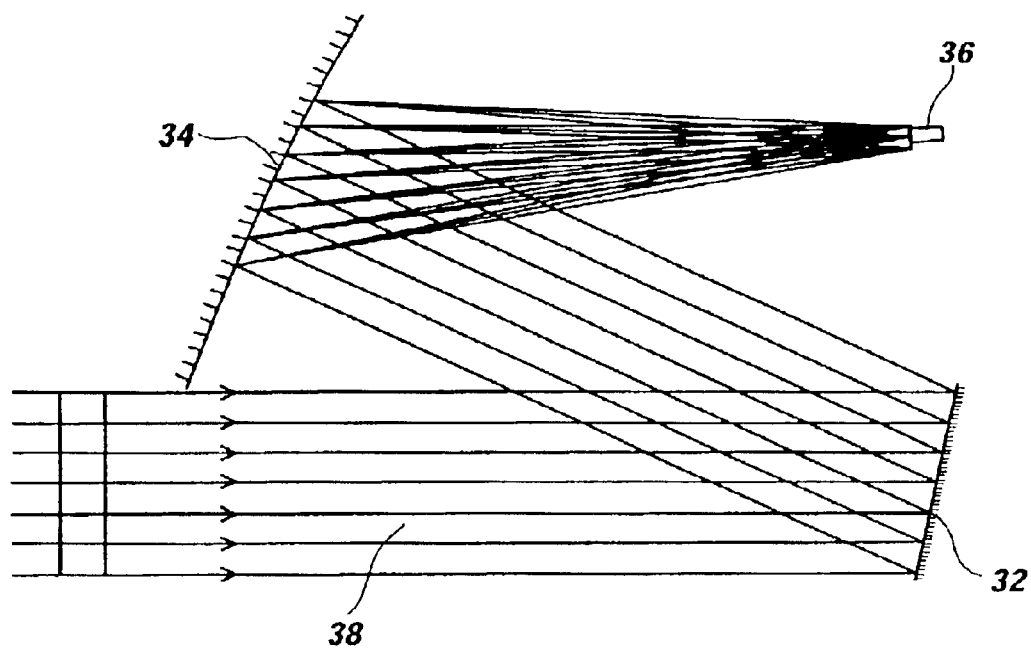
FIG. 3 is a schematic optical system layout for a spectrometer with a focusing mirror-diffraction grating combination according to the present invention.

The schematic illustrated in FIG. 1A uses scanning grating reflector 14 as both scanner and diffraction grating. However, it is not necessary to include the diffraction grating on the scanner. The diffraction grating may be scanned in angle by a mirror scanner instead. As shown in FIG. 3, a mirror scanner 32 is used to sweep the input beam 30 from the gas sample cell over the diffraction grating and mirror combination 34. The mirror employed in diffraction grating and mirror combination 34 is a focusing element that directs and focuses dispersed energy from mirror scanner 32 to the detector 36. The image formed is of the defining input aperture, in the wavelength selected by the diffraction grating and mirror combination 34. In a conventional Ebert monochrometer, there is a slit at the entrance to the monochrometer that defines the aperture to be imaged. In the present invention, the defining aperture may be the source, or it may be a separate aperture near the entrance to the scanner/detector assembly. It should be noted that the turning mirror 12 of the embodiment of FIG. 1A does not have a structural counterpart in FIG. 3, as the turning mirror is not a required component of the invention, but is common in the prior art and use thereof does provide a number of other configuration possibilities.

As another alternative configuration, the mirror—grating function may be split up, such that the scan is directed to a flat grating mirror, followed by a focusing element, usually a mirror in this IR wavelength region, followed by the detector. The advantage of such alternative split configuration over the FIG. 1A configuration is that the scanning mirror device is directly manufacturable by presently known processes, while forming a grating on the mirror is not conventional. In contrast, forming a grating on a focusing element by molding techniques is conventional. The disadvantages of the split configuration are that the grating must be somewhat larger (because the beam moves across the grating in order to change the angle), and the mirror may need to be an asphere. These are minor issues if, as expected, the grating-mirror is made by a molding or casting process.

The embodiments described with respect to FIGS. 1A and 3 provide an effective way to collect spectral data over a wavelength octave. However, these embodiments are designed with a single band, such as, for example, the 3 to 5 micron band, in mind.

The range of a grating spectrometer is limited in a practical sense to an octave, because of multiple orders. That is, a particular wavelength will diffract at a certain set of angles, which depend on the wavelength, the grating period, and an integral number known as the Order. Because the dispersion is a function of the Order, multiple orders can overlap at the detector plane, making spectra difficult to interpret. In practical grating spectrometers, the grating is made so that most of the diffracted energy is directed to a particular desired order. This is done by contouring the surface at each groove of the diffraction grating so that light striking that point will be reflected in the same direction as the desired diffraction order. This contouring process is referred to as blazing. In addition, blocking filters may be added at the spectrometer input or at the detector that will block wavelength regions that might otherwise cause confusion.

In addition to the 3 to 5 micron band described earlier, it is advantageous for the present invention to measure the 7 to 10 micron range simultaneously. The problems in this longer wavelength range are that, first, a more expensive detector is required, second, transmission optics, e.g., lenses, for beam manipulation tend to be more expensive (although a longwave pass filter or function is unavoidable) and third, the second order of the 3 to 5 micron band would tend to fall in the same plane as the 7 to 10 micron band.

Seven exemplary approaches to optical arrangements for the measurement of additional bands are shown in FIGS. 4A through 4F. Note that in all illustrated cases shown in FIG. 4A through FIG. 4F, the input beam has already been collimated, either by the source optics, or by other conventional means. Note also that the drawings are schematic, i.e., the diffraction angles are illustrative and not exact.

Figure 4A:
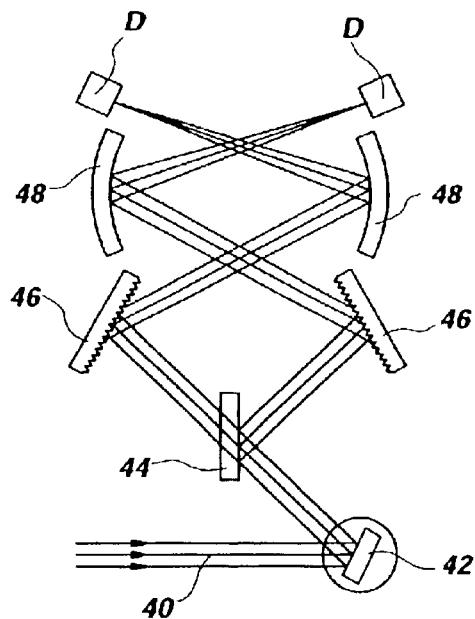
FIGS. 4A through 4F comprise schematics of a number of exemplary layouts for spectrometers using collimated light beams, enabling analysis of a plurality of spectral bands in accordance with the principles of the present invention.

In the embodiment of FIG. 4A, a scanning mirror 42 directs the input beam 40 to a dichroic beam splitter 44, which divides the beam into two bands, e.g., 3 to 5 and 7 to 10 microns, respectively. Two separate scanning diffraction gratings 46 disperse the bands; each grating 46 being optimized for a respective band. After dispersion, each band of the beam is directed by a focusing mirror 48 onto an aperture of a detector D.

Figure 4B:
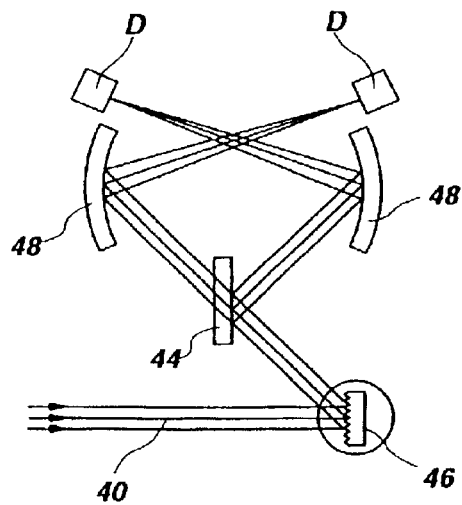

In the embodiment of FIG. 4B, a scanning diffraction grating 46 is employed, and the resultant dispersed beam is divided by a dichroic beam splitter 44 into two bands. In this case, the scanning diffraction grating 46 has been optimized for the 7–10 micron band in first order, and also for the 3–5 micron band in second order.

Figure 4C:
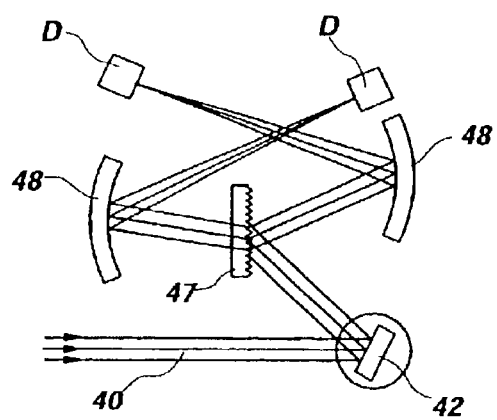

FIG. 4C illustrates an embodiment including a scanning mirror 42, followed by a dichroic diffraction grating 47 that is coated to reflect one band, such as 7–10 microns, and transmit the other. As in other cases, the dichroic diffraction grating 47 would be arranged for first order 7–10 microns, and second order 3–5 microns. Alternatively, a reflective diffraction grating (non-transmissive) may be employed, and a band splitter located after the diffraction grating.

Figure 4D:
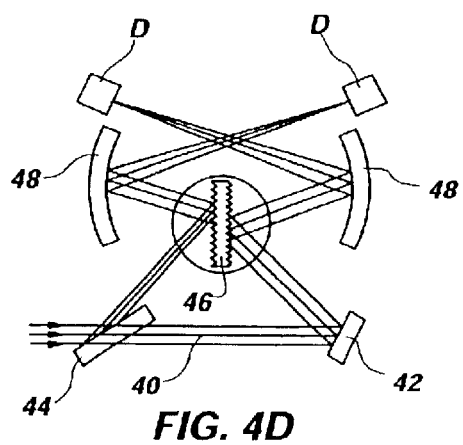

The embodiment of FIG. 4D uses back-to-back scanning diffraction gratings 46 that only reflect, and together are used as the scanning element. Band splitting is effected by a dichroic beam splitter 44 before the gratings. In this embodiment the gratings may be individually optimized for best performance in specific bands.

Figure 4E:
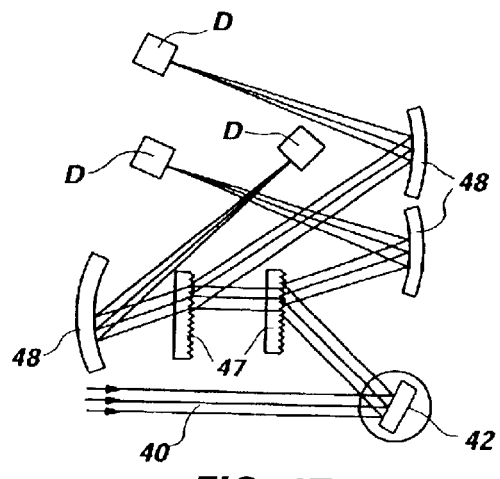

The embodiment of FIG. 4E is arranged to provide detection in three bands. The scanning mirror 42 illuminates two reflection/transmission dichroic diffraction gratings 47 in series. While this arrangement causes some restrictions on wavelength band placement, it is physically more compact than that of FIG. 4F.

Figure 4F:
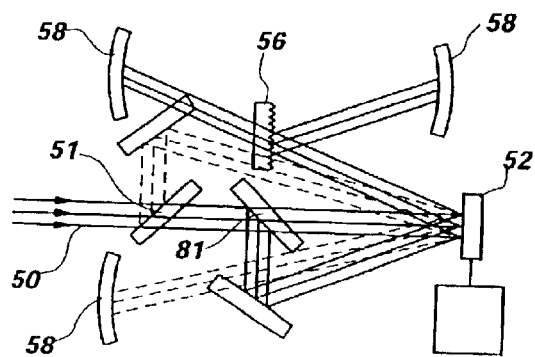

The embodiment of FIG. 4F includes a three-dimensional arrangement of mirrors and gratings that can provide six bands (as shown), and more bands by extension. The input beam 50 is first split into three wavelength blocks of two contiguous octave bands each using multiple dichroic or bandpass filters 51, which wavelength blocks are then scanned by a scanning mirror 52. The axis of the scanning mirror 52 is in the plane of the drawing sheet. The wavelength blocks are geometrically separated by angle in a plane that includes the mirror rotation axis. After scanning, the wavelength blocks go to three diffraction gratings 56, each similar to that FIG. 4C but suitably tilted to match the separation angle. Note that only one grating 56, and no detectors, are shown for simplicity and clarity of illustration in FIG. 4F, although such would be included in practice.

Figure 5A:
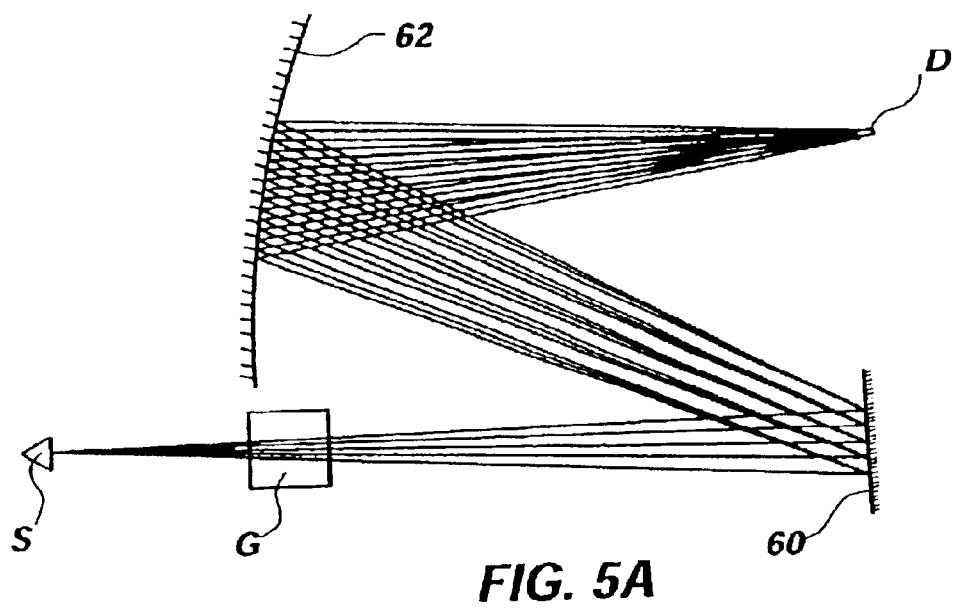
FIGS. 5A through 5C comprise schematics of a number of exemplary layouts for spectrometers using non-collimated light beams, enabling analysis of a plurality of spectral bands in accordance with the principles of the present invention.
Figure 5B:
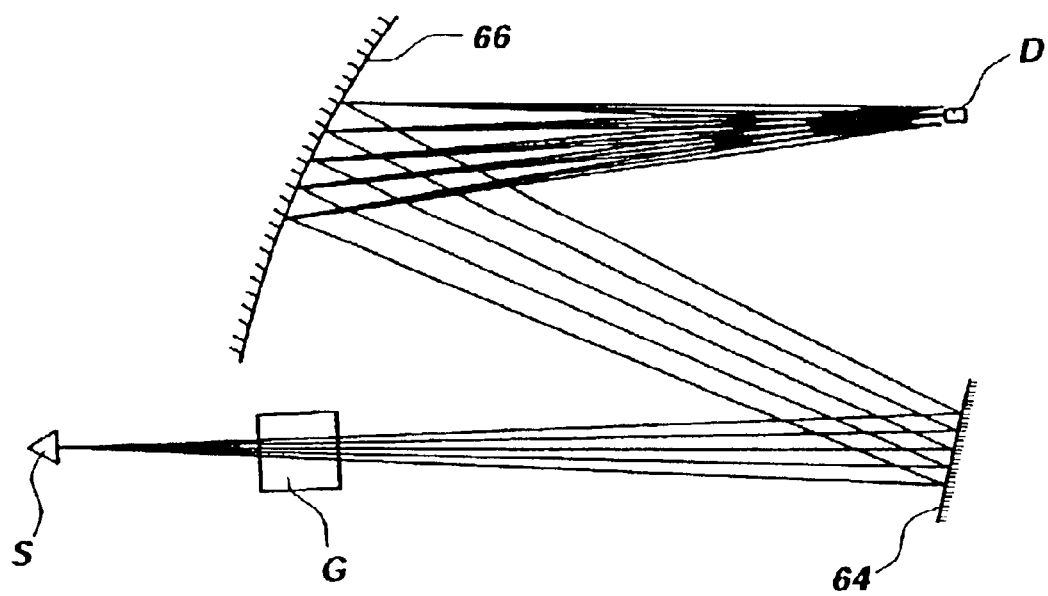
Figure 5C:
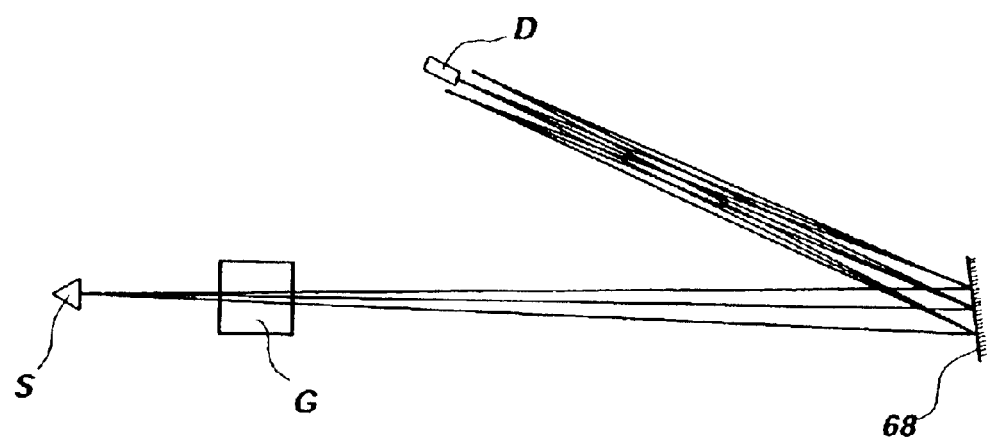

FIGS. 5A through 5C depict additional embodiments of the present invention wherein, unlike those described above, light entering the spectrometer may be diverging or converging and the optics modified to compensate therefore.

FIG. 5A schematically depicts a system wherein light from a source S passes through gas sample cell G and is reflected, dispersed by a grating and scanned on a scanning flat grating mirror 60. The resultant dispersed light beam is focused using a concave mirror 62 onto detector D.

FIG. 5B schematically depicts a system using a flat scanning mirror 64, and the scanned beam is reflected to a concave grating mirror 66 that diffracts and focuses the light beam onto detector D.

FIG. 5C schematically depicts a system wherein the scanning, dispersion and focusing functions are consolidated into a single element 68 in the form of a scanning mirror which includes a diffraction grating and is concave for focusing the light beam onto detector D.

As will be understood and appreciated by those of ordinary skill in the art, adding functions to a scanning element increases the cost thereof, but in each instance other elements in a system may be reduced in cost, or eliminated entirely. In particular, the embodiments of FIGS. 5A through 5C eliminate the need for collimating elements, and the embodiment of FIG. 5C eliminates the need for a separate focusing mirror. Such reductions in the number of required components enable the fabrication of a less costly system due both to elimination of components and a reduction in assembly time.

It will also be understood and appreciated by those of ordinary skill in the art, the approaches illustrated in FIGS. 5A through 5C may be applied to the embodiments of FIGS. 4A through 4F for the measurement of multiple bands of interest. For example, the components and arrangement of FIG. 5A may be advantageously employed to modify the systems of FIGS. 4B and 4D, while the components and arrangement of FIG. 5B may be advantageously employed to modify the system of FIG. 4A, in each instance resulting in the elimination of a focusing mirror. The components and arrangement of FIG. 5B may also be employed in the systems of FIGS. 4C, 4E and 4F, although the focusing mirror and grating element would be more complex, since it would be required to focus in both reflection and transmission. The first, or reflecting, face would be concave, while the second face would comprise a convex refracting face.

While the spectrometer of the present invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. A spectrometer comprising:
   an infrared source for projecting an infrared beam;
   a gas sample cell positioned in the path of the infrared beam;
   a scanning mirror bearing a diffraction grating comprising a plurality of parallel lines and positioned in the path of the infrared beam after passage thereof through the gas sample cell;
   a mirror drive for oscillating the scanning mirror about an axis parallel to the diffraction grating lines;
   a first focusing mirror positioned to focus at least one band of interest of the infrared beam as diffracted by the diffraction grating;
   a first detector positioned to receive the at least one focused band of interest;
   a first detector readout circuit operatively coupled to the first detector to receive a signal from the first detector; and
   a synchronizer operatively coupled to the mirror drive and the detector readout circuit, wherein the synchronizer is adapted to synchronize oscillation of the scanning mirror with an output of the first detector readout circuit.

2. The spectrometer of claim 1, wherein the mirror drive is an electrostatic drive or a magnetic drive.

3. The spectrometer of claim 1, wherein the synchronizer is a phase lock loop synchronizer programmed to locate a preselected spectral region of interest from the output of the first detector readout circuit.

4. The spectrometer of claim 1, wherein the synchronizer is responsive to a signal received from the mirror drive.

5. The spectrometer of claim 1, further comprising a sensor mounted in proximity to the scanning mirror for determining positions of the scanning mirror to provide an input signal to the synchronizer.

6. The spectrometer of claim 1, further comprising a turning mirror, positioned to reflect the infrared beam toward the scanning mirror after the beam passes through the gas sample cell.

7. The spectrometer of claim 6, wherein the turning mirror is positioned to reflect the infrared beam through the gas sample cell a second time before the infrared beam reaches the scanning mirror.

8. The spectrometer of claim 1, further including a collimator positioned to receive and collimate the infrared beam projected from the source.

9. The spectrometer of claim 1, further comprising:
   a dichroic splitter positioned in the path of the diffracted infrared beam from the scanning mirror for separating the diffracted infrared beam into discrete bands of interest traveling respective paths;
   a second focusing mirror positioned in a respective path of the discrete bands of interest;
   a second detector positioned to receive a focused discrete band of interest; and
   a second detector readout circuit operatively coupled to the second detector to receive a signal from the second detector, wherein the synchronizer is adapted to synchronize oscillation of the scanning mirror with an output of at least one of the first and the second detector readout circuits.

10. The spectrometer of claim 9, wherein the mirror drive is an electrostatic drive or a magnetic drive.

11. The spectrometer of claim 9, wherein the synchronizer is a phase lock loop synchronizer programmed to locate a preselected spectral region of interest from the output of the first or the second detector readout circuits.

12. The spectrometer of claim 9, wherein the synchronizer is responsive to a signal received from the mirror drive.

13. The spectrometer of claim 9, further comprising a sensor mounted in proximity to the scanning mirror for determining positions of the scanning mirror to provide an input signal to the synchronizer.

14. The spectrometer of claim 9, further comprising a turning mirror, positioned to reflect the infrared beam toward the scanning mirror after the beam passes through the gas sample cell.

15. The spectrometer of claim 14, wherein the turning mirror is positioned to reflect the infrared beam through the gas sample cell a second time before the infrared beam reaches the scanning mirror.

16. The spectrometer of claim 9, further including a collimator positioned to receive and collimate the infrared beam projected from the source.

17. The spectrometer of claim 1, wherein the scanning mirror is a scanning flat grating mirror.

18. The spectrometer of claim 17, wherein the mirror drive is an electrostatic drive or a magnetic drive.

19. The spectrometer of claim 17, wherein the synchronizer is a phase lock loop synchronizer programmed to locate a preselected spectral region of interest.

20. The spectrometer of claim 17, wherein the synchronizer is responsive to a signal received from the mirror drive.

21. The spectrometer of claim 17, further comprising a sensor mounted in proximity to the scanning flat grating mirror for determining positions of the scanning mirror to provide an input signal to the synchronizer.

22. The spectrometer of claim 17, further comprising a turning mirror, positioned to reflect the infrared beam toward the scanning flat grating mirror after the infrared beam passes through the gas sample cell.

23. The spectrometer of claim 22, wherein the turning mirror is positioned to reflect the infrared beam through the gas sample cell a second time before the infrared beam reaches the scanning flat grating mirror.

24. The spectrometer of claim 1, wherein the scanning mirror is a concave scanning and focusing mirror to focus at least one band of interest of the infrared beam as diffracted by the diffraction grating.

25. The spectrometer of claim 24, wherein the mirror drive is an electrostatic drive or a magnetic drive.

26. The spectrometer of claim 24, wherein the synchronizer is a phase lock loop synchronizer programmed to locate a preselected spectral region of interest.

27. The spectrometer of claim 24, wherein the synchronizer is responsive to a signal received from the mirror drive.

28. The spectrometer of claim 24, further comprising a sensor mounted in proximity to the scanning mirror for determining positions of the concave scanning and focusing mirror to provide an input signal to the synchronizer.

29. The spectrometer of claim 24, further comprising a turning mirror, positioned to reflect the infrared beam toward the concave scanning and focusing mirror after the beam passes through the sample cell.

30. The spectrometer of claim 24, wherein the turning mirror is positioned to reflect the infrared beam through the gas sample cell a second time before the infrared beam reaches the concave scanning and focusing mirror.

31. A spectrometer comprising:
   an infrared source for projecting an infrared beam;
   a gas sample cell positioned in the path of the infrared beam;
   a scanning mirror positioned in the path of the infrared beam after passage thereof through the gas sample cell;
   a mirror drive for oscillating the scanning mirror;
   a first focusing mirror bearing a diffraction grating comprising a plurality of parallel lines, wherein the first focusing mirror is positioned in the path of the infrared beam reflected from the scanning mirror for reflecting, diffracting, and focusing a band of interest from the infrared beam;
   a first detector positioned in the path of the band of interest;
   a first detector readout circuit operatively coupled to the first detector to receive a signal from the first detector; and
   a synchronizer operatively coupled to the mirror drive and the detector readout circuit, wherein the synchronizer is adapted to synchronize oscillation of the scanning mirror with an output of the first detector readout circuit.

32. The spectrometer of claim 31, wherein the mirror drive is an electrostatic drive or a magnetic drive.

33. The spectrometer of claim 31, wherein the synchronizer is a phase lock loop synchronizer programmed to locate a preselected spectral region of interest from the output of the first detector readout circuit.

34. The spectrometer of claim 31, wherein the synchronizer is responsive to a signal received from the mirror drive.

35. The spectrometer of claim 31, further comprising a sensor mounted in proximity to the scanning mirror for determining positions of the scanning mirror to provide an input signal to the synchronizer.

36. The spectrometer of claim 31, further comprising a turning mirror, positioned to reflect the infrared beam toward the scanning mirror after the beam passes through the sample cell.

37. The spectrometer of claim 36, the turning mirror is positioned to reflect the infrared beam through the gas sample cell a second time before the infrared beam reaches the scanning mirror.

38. The spectrometer of claim 31, further including a collimator positioned to receive and collimate the infrared beam projected from the source.

39. The spectrometer of claim 31, further comprising:
   a dichroic splitter positioned in the path of the infrared beam reflected from the scanning mirror for splitting the infrared beam into a plurality of bands of interest;
   a second focusing mirror bearing a diffraction grating comprising a plurality of lines, wherein the second focusing mirror positioned in a path of a band of interest for reflecting, diffracting, and focusing a respective band of interest;
   a second detector positioned to receive a reflected, focused band of interest; and
   a second detector readout circuit operatively coupled to the first or the second detector to receive a signal from the first or the second detector, wherein the synchronizer is adapted to synchronize oscillation of the scanning mirror with an output of at least one of the first and the second detector readout circuits.

40. The spectrometer of claim 39, wherein the mirror drive is an electrostatic drive or a magnetic drive.

41. The spectrometer of claim 39, wherein the synchronizer is a phase lock loop synchronizer programmed to locate a preselected spectral region of interest from the output of the first or the second detector readout circuits.

42. The spectrometer of claim 39, wherein the synchronizer is responsive to a signal received from the mirror drive.

43. The spectrometer of claim 39, further comprising a sensor mounted in proximity to the scanning mirror for determining positions of the scanning mirror to provide an input signal to the synchronizer.

44. The spectrometer of claim 39, further comprising a turning mirror, positioned to reflect the infrared beam toward the scanning mirror after the infrared beam passes through the gas sample cell.

45. The spectrometer of claim 44, wherein the turning mirror is positioned to reflect the infrared beam through the gas sample cell a second time before the infrared beam reaches the scanning mirror.

46. The spectrometer of claim 39, further including a collimator positioned to receive and collimate the infrared beam projected from the source.

47. The spectrometer of claim 31, wherein the scanning mirror is a scanning flat mirror.

48. The spectrometer of claim 47, wherein the mirror drive is an electrostatic drive or a magnetic drive.

49. The spectrometer of claim 47, wherein the synchronizer is a phase lock loop synchronizer programmed to locate a preselected spectral region of interest.

50. The spectrometer of claim 47, wherein the synchronizer is responsive to a signal received from the mirror drive.

51. The spectrometer of claim 47, further comprising a sensor mounted in proximity to the scanning flat mirror for determining positions of the scanning mirror to provide an input signal to the synchronizer.

52. The spectrometer of claim 47, further comprising a turning mirror, positioned to reflect the infrared beam toward the scanning flat mirror after the beam passes through the gas sample cell.

53. The spectrometer of claim 52, wherein the turning mirror is positioned to reflect the infrared beam through the gas sample cell a second time before the infrared beam reaches the scanning flat mirror.

54. A spectrometer comprising:
an infrared source for projecting an infrared beam;
a gas sample cell positioned in the path of the infrared beam;
a scanning mirror positioned in the path of the infrared beam after passage thereof through the gas sample cell;
a mirror drive for oscillating the scanning mirror;
a first diffraction grating positioned in the path of the infrared beam as reflected from the scanning mirror for diffracting the infrared beam;
a first focusing mirror positioned in the path of a portion of the diffracted infrared beam to focus a band of interest;
a first detector positioned to receive a focused band of interest;
a first detector readout circuit operatively coupled to the first detector to receive a signal from the first detector; and
a synchronizer operatively coupled to the mirror drive and the first detector readout circuit, wherein the synchronizer is adapted to synchronize oscillation of the scanning mirror with an output of the first detector readout circuit.

55. The spectrometer of claim 54, wherein the mirror drive is an electrostatic drive or a magnetic drive.

56. The spectrometer of claim 54, wherein the synchronizer is a phase lock loop synchronizer programmed to locate a preselected spectral region of interest from the output of the first detector readout circuit.

57. The spectrometer of claim 54, wherein the synchronizer is responsive to a signal received from the mirror drive.

58. The spectrometer of claim 54, further comprising a sensor mounted in proximity to the scanning mirror for determining positions of the scanning mirror to provide an input signal to the synchronizer.

59. The spectrometer of claim 54, further comprising a turning mirror, positioned to reflect the infrared beam toward the scanning mirror after the beam passes through the sample cell.

60. The spectrometer of claim 59, wherein the turning mirror is positioned to reflect the infrared beam through the gas sample cell a second time before the infrared beam reaches the scanning mirror.

61. The spectrometer of claim 54, further including a collimator positioned to receive and collimate the infrared beam projected from the source.

62. The spectrometer of claim 54, further comprising:
a first dichroic splitter positioned to receive the infrared beam reflected from the scanning mirror and divide the infrared beam into a plurality of bands;
a second diffraction grating positioned to receive at least one band of interest from the first dichroic splitter;
a second focusing mirror positioned in the path of the at least one band of interest after diffraction thereof;
a second detector positioned in the path of the at least one diffracted band of interest focused by the second focusing mirror; and
a second detector readout circuit, wherein the synchronizer is adapted to synchronize oscillation of the scanning mirror with an output of at least one of the first and the second detector readout circuits.

63. The spectrometer of claim 62, wherein the mirror drive is an electrostatic drive or a magnetic drive.

64. The spectrometer of claim 62, wherein the synchronizer is a phase lock loop synchronizer programmed to locate a preselected spectral region of interest from the output of the first or the second detector readout circuits.

65. The spectrometer of claim 62, wherein the synchronizer is responsive to a signal received from the mirror drive.

66. The spectrometer of claim 62, further comprising a sensor mounted in proximity to the scanning mirror for determining positions of the scanning mirror to provide an input signal to the synchronizer.

67. The spectrometer of claim 62, further comprising a turning mirror, positioned to reflect the infrared beam toward the scanning mirror after the beam passes through the gas sample cell.

68. The spectrometer of claim 67, wherein the turning mirror is positioned to reflect the infrared beam through the gas sample cell a second time before the infrared beam reaches the scanning mirror.

69. The spectrometer of claim 62, further including a collimator positioned to receive and collimate the infrared beam projected from the source.

70. The spectrometer of claim 62, further comprising:
a third diffraction grating positioned to receive at least one band of interest from the first or the second dichroic splitter;
a third focusing mirror positioned in the path of a band of interest after diffraction thereof;
a third detector positioned in the path of a diffracted band of interest focused by one of the first, the second, or the third focusing mirror; and
a third detector readout circuit operatively coupled to the first, the second, or the third detector to receive a signal from the first, the second, or the third detector, wherein the synchronizer is adapted to synchronize oscillation of the scanning mirror with one of the first, the second, and the third detector readout circuits.

* * * * *